(12) United States Patent
Nguyen et al.

(10) Patent No.: US 9,220,807 B2
(45) Date of Patent: Dec. 29, 2015

(54) NON-TOXIC CROSS-LINKER FOR HYALURONIC ACID

(71) Applicants: Phi Nguyen, Houston, TX (US); Loc Phan, San Jose, CA (US); Bao Tran, Saratoga, CA (US); Thuan Nguyen, Houston, CA (US); Duy Bui, Ha Noi (VN)

(72) Inventors: Phi Nguyen, Houston, TX (US); Loc Phan, San Jose, CA (US); Bao Tran, Saratoga, CA (US); Thuan Nguyen, Houston, CA (US); Duy Bui, Ha Noi (VN)

(73) Assignee: MIBA Medical Inc., San Jose, CA (US)

( * ) Notice: Subject to any disclaimer, the term of this patent is extended or adjusted under 35 U.S.C. 154(b) by 0 days.

(21) Appl. No.: 14/255,967

(22) PCT Filed: Apr. 12, 2013

(86) PCT No.: PCT/VN2013/000004
§ 371 (c)(1),
(2) Date: May 1, 2014

(87) PCT Pub. No.: WO2014/169301
PCT Pub. Date: Oct. 16, 2014

(65) Prior Publication Data
US 2015/0297789 A1  Oct. 22, 2015

Related U.S. Application Data

(60) Provisional application No. 61/722,221, filed on Nov. 4, 2012.

(51) Int. Cl.
*A61F 2/12* (2006.01)
*A61L 27/20* (2006.01)
*A61L 27/50* (2006.01)
*A61L 27/54* (2006.01)
*A61L 27/52* (2006.01)

(52) U.S. Cl.
CPC . *A61L 27/20* (2013.01); *A61F 2/12* (2013.01); *A61L 27/50* (2013.01); *A61L 27/52* (2013.01); *A61L 27/54* (2013.01); *A61L 2300/402* (2013.01); *A61L 2300/41* (2013.01); *A61L 2300/416* (2013.01); *A61L 2300/602* (2013.01); *A61L 2400/06* (2013.01); *A61L 2400/18* (2013.01); *A61L 2430/34* (2013.01)

(58) Field of Classification Search
CPC .... A61K 38/363; A61K 9/0024; A61F 2/027; A61F 2/12; A61L 31/146
USPC ........................ 623/11.11–1.44, 23.65–23.76
See application file for complete search history.

(56) References Cited

U.S. PATENT DOCUMENTS

| | | | |
|---|---|---|---|
| 4,538,920 A | 9/1985 | Drake | |
| 5,219,360 A | 6/1993 | Georgiade | |
| 6,881,226 B2 * | 4/2005 | Corbitt, Jr. | ................ A61F 2/12 424/400 |
| 7,998,201 B2 * | 8/2011 | Lesh | ..................... A61F 2/0059 623/11.11 |
| 7,998,202 B2 * | 8/2011 | Lesh | ..................... A61F 2/0059 623/11.11 |
| 8,383,161 B2 * | 2/2013 | Campbell | ............... A61L 27/50 424/502 |
| 9,039,763 B2 * | 5/2015 | Corbitt, Jr. | ................ A61F 2/12 623/7 |

(Continued)

*Primary Examiner* — Suzette J Gherbi
(74) *Attorney, Agent, or Firm* — Tran & Associates (57) ABSTRACT

Systems and methods are disclosed for cosmetic augmentation by storing a non-toxic biocompatible cross-linker; storing a biocompatible polymer having a multi-phase mixture with a predetermined controlled release of selected pharmaceutical substance to modulate soft tissue response to the polymer; mixing the biocompatible cross-linker and polymer into a mixture; injecting the mixture into a patient and during or after injection, cross-linking the polymer in the patient; and augmenting soft tissue with the biocompatible cross-linked polymer.

23 Claims, 5 Drawing Sheets

(56) References Cited

U.S. PATENT DOCUMENTS

| | | | |
|---|---|---|---|
| 2004/0006296 A1* | 1/2004 | Fischell | A61B 17/06166 602/48 |
| 2004/0047892 A1* | 3/2004 | Desrosiers | A61L 27/20 424/423 |
| 2005/0187639 A1* | 8/2005 | Hunter | A61K 38/17 623/23.72 |
| 2007/0212385 A1 | 9/2007 | David | |
| 2008/0159608 A1* | 7/2008 | Suetens | G06T 7/0018 382/128 |
| 2008/0228268 A1 | 9/2008 | Shannon | |
| 2009/0181104 A1* | 7/2009 | Rigotti | A61K 35/35 424/574 |
| 2011/0142936 A1* | 6/2011 | Campbell | A61L 27/50 424/484 |
| 2011/0150846 A1* | 6/2011 | Van Epps | A61L 27/3839 424/93.7 |
| 2012/0039980 A1* | 2/2012 | Daniloff | A61K 9/1075 424/422 |
| 2012/0128746 A1* | 5/2012 | Maitra | A61K 8/891 424/401 |
| 2012/0165935 A1* | 6/2012 | Van Epps | A61L 27/3839 623/8 |
| 2012/0208890 A1 | 8/2012 | Gousse | |
| 2013/0012683 A1* | 1/2013 | Daniloff | A61K 9/0024 528/372 |
| 2013/0273115 A1* | 10/2013 | Nguyen | A61K 9/0014 424/400 |
| 2014/0329756 A1* | 11/2014 | Nguyen | A61K 9/0024 514/17.2 |
| 2015/0190517 A1* | 7/2015 | Nguyen | A61K 31/167 514/180 |

\* cited by examiner

| |
|---|
| storing a non-toxic biocompatible cross-linker in a first volume (702) |
| storing in a second volume a biocompatible polymer having a multi-phase mixture with a predetermined controlled release of selected pharmaceutical substance to modulate soft tissue response to the polymer (704) |
| mixing the biocompatible cross-linker and polymer into a mixture (706) |
| injecting the mixture into a patient and during or after injection, cross-linking the polymer in the patient (708) |

FIG. 5

| |
|---|
| Forming a cross-linked filler composition having a biocompatible, biodegradable, nontoxic properties, the filler composition having a predetermined radiolucency greater than silicone or saline radiolucency (802) |
| Injecting the mixture as separate phases into the body and mixing the mixture during the injection process to cause cross-linking of the multiphase mixture (803) |
| Introducing the filler composition into a shell or an envelope of a soft tissue human implant prior to or during implantation of the shell or envelope into a lumen in a human body (804) |
| Cross-linking the filler composition, and the cross linking reaction occurs outside the shell/envelope or in-situ inside the shell/envelope (810) |

FIG. 6

NON-TOXIC CROSS-LINKER FOR HYALURONIC ACID

This application claims priority to Provisional Application Ser. 61/722,221 filed Nov. 4, 2012, and PCT Application Serial PCT/VN2013/000001 filed Apr. 12, 2013, PCT/VN2013/000002 filed Apr. 12, 2013, PCT/VN2013/000003 filed on Apr. 12, 2013, PCT/VN2013/000004 filed Apr. 12, 2013, and PCT/VN2012/000008 filed Dec. 17, 2012, the contents of which are incorporated by reference.

BACKGROUND

The present invention relates to biodegradable hyaluronic acid filler compositions for soft tissue implants and body augmentation such as dermal fillers or breast, butt or body implants.

Everyone wants healthy and younger-looking skin. Having smooth skin and youthful appearance can make a person appear years younger, feel beautiful and more self-assured. Injectable dermal implants are a popular solution to correct a wide variety of facial contour defects that are congenital or as a result of serious accidents. The injectable dermal implants are very effective in cosmetic surgery procedures such as lip augmentation and scar removal.

Generally, as the years take its tolls on the body, the cells that generate the connective tissues that makeup the scaffold of the body become less efficient, and cannot keep up with the daily repair processes. Thus, our skin loses resiliency, elasticity and from which onsets wrinkles. The gerontological process happens at seemingly exponential speed.

The concept of biocompatibility is moving from a "do-no-harm" mission (i.e., nontoxic, non-antigenic, non-mutagenic, etc.) to one of "doing-good," that is, encouraging positive healing responses. These new devices will promote the formation of normal healthy tissue as well as the integration of the device into adjacent tissue. In some contexts, biocompatibility can become a disruptive technology that can change therapeutic paradigms (e.g., drug-coated stents).

The required material properties are determined by the specific device application and the functional life of the device, which ranges from temporary use to permanent implant. Devices can be used in:

1. blood-contacting applications such as extracorporeal devices that remove and return blood from the body, devices that are inserted into a blood vessel, or devices that are permanently implanted.

2. soft-tissue device applications, such as soft-tissue augmentation;

3. orthopedic and dental applications for joint, bone, and tooth replacement and repair 4. specific organ applications (e.g., neural); and 5. scaffolds for tissue engineering for tissue and organ replacement.

Development of an injectable hydrogel for tissue repair or tissue regeneration presents considerable challenges. The gelation conditions for in vivo use are limited to a narrow range of physiologically acceptable temperatures, and the crosslinking must occur with no by-products in a sensitive aqueous environment. Reagents must be nontoxic reagents and tolerant of moist, oxygen-rich environments. Furthermore, gelation must occur at a sufficiently rapid rate for clinical use in an outpatient or operating suite setting, yet sufficiently slow that complete mixing occurs prior to gelation.

In a parallel trend, millions of women have undergone breast, butt or body augmentation and reconstruction in the past few decades. Most women choose augmentation to enhance the size and shape of one or both breast, butt or body parts for personal or aesthetic reasons. In contrast, women who undergo a reconstruction procedure want to reconstruct a breast, butt or body that has been removed, typically for health reasons, such as tumor removal. The reconstruction procedure may vary from a modified radical mastectomy (removal of the underlying muscle as well as the breast, butt or body), to a simple mastectomy (removal of one breast, butt or body), to a bilateral mastectomy (removal of breast, butt or body parts) or to a lumpectomy (removal of a portion of the breast, butt or body). In either augmentation or reconstruction, the modality intimates the surgical implantation of breast, butt or body prosthesis (implant).

Conventional implants for treating breast, butt or body augmentation or reconstruction include a shell or envelope that is filled with a filler composition, for example, silicone gel, saline solution, or other suitable filler. It is desirable that the filler have lubricating properties to prevent shell abrasion, remain stable over long periods of time, be non-carcinogenic and non-toxic, and have physical properties to prevent skin wrinkling, capsular contracture formation, and implant palpability.

While breast, butt or body implants containing silicone-gel as a filler are widely used for breast, butt or body augmentation or reconstruction, a variety of potential disadvantages have been recognized with respect to the stabilization of the implants and the immune system. First, the silicone gel-filled implants have a tendency to leak. In 1992, the FDA issued a voluntary moratorium on silicone gel-filled implants due to public health concerns regarding the potential link between leaking silicone gel-filled implants and autoimmune diseases. To date, the long term effect of silicone-gel on the immune system is still unknown. Second, the leaking of the implants necessitates the need for additional surgeries for removal or repair of the implants. Third, the silicone-gel as a filling material has a greater density than saline or natural tissues which may cause recipients back pain. Fourth, silicone is a permanent filler composition and when it leaks, it can travel though out the body and can cause unwanted hard nodular formations if left untreated. Lastly, the silicone-gel implant although currently the state of the art, it does not mimic the touch and feel of a real breast, butt or body. It offers a more realistic feel than saline as a filler material.

Many plastic surgeons turned to saline as an alternative replacement for silicone-gel. Several implants which use saline are known and were found to be advantageous over silicone-gel for several reasons. Saline has a lower density than silicone-gel causing less strain on recipients' backs. In addition, if the implant leaks, the saline solution is biocompatible providing a more tolerated and safer implant than those containing silicone-gel.

However, while the saline implant offer significant advantages over the silicone-gel implant, various problems have been encountered. Implants using saline are disadvantageous in that they frequently result in capsular contraction, a phenomenon where the body forms a lining of fibrous tissue encapsulating the breast, butt or body implant and the resulting capsule tightens and squeezes the implant. Symptoms range from mild firmness and mild discomfort to severe pain, distorted shape, palpability of the implant, and/or movement of the implant. Additional surgery may be needed in cases where pain and/or firmness are severe. This surgery ranges from removal of the implant capsule tissue to removal and possibly replacement of the implant itself. There is no guarantee that capsular contracture will not occur after these additional surgeries.

Saline implants may have to be removed and replaced periodically for other reasons—they fracture or they deflate. Saline, because it is less viscous than silicone-gel, settles in the bottom portion of the implant when the recipient is upright. This leaves the upper portion of the implant prone to excessive folding or wrinkling, causing stress fracturing of the shell at the fold points. Furthermore, the saline-filled implants have a tendency to drain gradually in about ten years. Barring any deflation or rupture complications, saline as a filler for breast, butt or body implants produces an unnatural feel and look to the implant.

U.S. Pat. No. 6,881,226 discloses a breast, butt or body implant having at least an outer shell which is composed of a resorbable material. The implant, which can be formed entirely of bioresorbable material such as collagen foam, is sized and shaped to replace excised tissue. The implant supports surrounding tissue upon implantation, while allowing for in-growth of fibrous tissue to replace the implant. According to various alternative embodiments, the implant is elastically compressible, or can be formed from self-expanding foam or sponges, and can be implanted through a cannula or by injection, as well as by open procedures. The implant can carry therapeutic and diagnostic substances.

In response to the failures of saline and silicone-gel implants, there have been a number of attempts to make a prosthesis filled with a non-toxic filler that that mimics the shape and feel of a natural breast, butt or body provided by silicone-gel yet is safe to the immune system like saline. Other attempts to provide a safe filler material include polyethylene glycol. However, the triglyceride oil or honey fails to provide an implant that is aesthetically pleasing and also duplicates the touch and feel of a natural breast, butt or body due to the low viscosity of the fillers. Due to the limited options and the inadequacy of current fillers to achieve the desired results, there is a need for safe and efficacious fillers.

SUMMARY

Systems and methods are disclosed for cosmetic augmentation by storing a non-toxic biocompatible cross-linker; storing a biocompatible polymer having a multi-phase mixture with a predetermined controlled release of selected pharmaceutical substance to modulate soft tissue response to the polymer; mixing the biocompatible cross-linker and polymer into a mixture; injecting the mixture into a patient and during or after injection, cross-linking the polymer in the patient; and augmenting soft tissue with the biocompatible cross-linked polymer.

In one aspect, systems and methods are disclosed for cosmetic augmentation by forming a biocompatible cross-linked polymer having a multi-phase mixture with a predetermined controlled release of selected pharmaceutical substance to modulate soft tissue response to the polymer; injecting the mixture into a patient and during or after injection, cross-linking the polymer in the patient; and augmenting soft tissue with the biocompatible cross-linked polymer.

In another aspect, systems and methods are disclosed for breast, butt or body implants by forming a biocompatible cross-linked polymer having a multi-phase mixture with a predetermined controlled release of selected pharmaceutical substance to modulate soft tissue response to the polymer; injecting the mixture into a patient and during or after injection, cross-linking the polymer in the patient; filling a semi-permeable shell with the pharmaceutical substance; and augmenting soft tissue with the biocompatible cross-linked polymer.

Implementations of the above aspects can include in-situ cross-linking of PEG and in-situ cross-linking of collagen. The cross linker can also be based on non-covalent bonding techniques such as hydrogen/oxygen, hydrogen/nitrogen association, charge, ionic interactions and/or polarity and their association states may change from being tightly associated to not at all associated as a function of local environmental condition changes such as slight differences in temperatures, pH's and/or osmolalities among others.

Advantages of the system may include one or more of the following. The flow properties are tailored for injection through a small bore needle. The system has greater flexibility to control physical properties of the final gel. The final gel could be tailored to have greater cohesive strength which will resist migration to another anatomical space. The final gel durometer could be tailored to be more natural, similar in feel and appearance to the surrounding tissue The final gel could be tailored to have properties similar to surround tissue. The longevity of the final gel could be tailored to meet various anatomical location requirements (longer biodegradation or shorter depending on anatomical location). The final gel physical properties stay constant over the life time of the material.

DESCRIPTION

Figure 1:
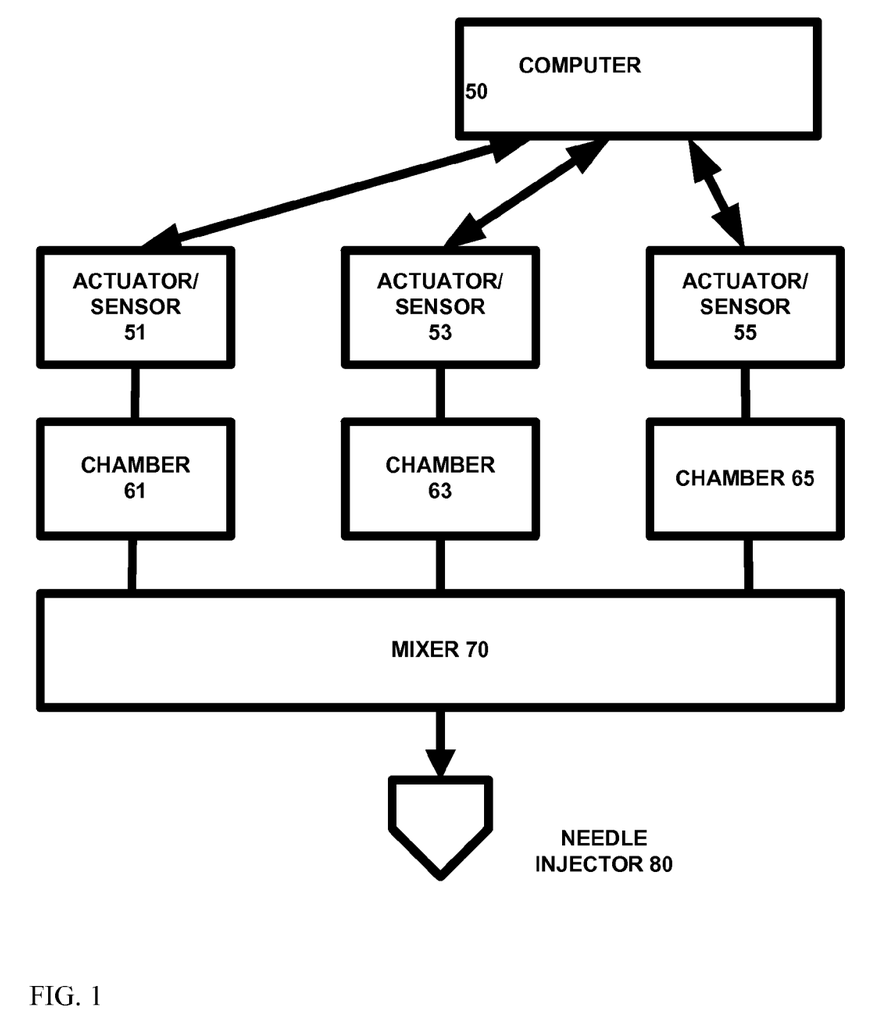
FIG. 1 shows an exemplary block diagram of a computer controlled hyaluronic acid (HA) injector system that cross-links the HA while the drug is injected into the body.

FIG. 1 shows an exemplary block diagram of a hyaluronic acid (HA) injector system that cross-links the HA while the drug is injected into the body. As shown therein, a triple cartridge with parallel container search housing one of three flowable components to be mixed when desired in a static mixer and which terminates in an outlet tip from which the components mixed by the static mixer are expelled. The static mixer may be separable from and attached to the containers or chambers in a manner known per se. The containers, usually made of a plastics material, are joined by a bridge defining an outlet in which the two components are separated by an internal dividing wall to maintain the components separate and unmixed until they reach inlet of the static mixer for mixing therein. In a conventional manner, the static mixer, again usually of a plastics material, comprises a static mixer element housed in an elongate member extending from attachment to the outlet to outlet tip. Also the static mixer element comprises an axially extending serial plurality of alternating oppositely oriented helically twisted mixer blades which act in concert to efficiently and thoroughly mix the separate components as they flow through the static mixer 6 from the outlet to the outlet tip. Pistons or motorized actuators are operated simultaneously by a suitable mechanism (not shown) with the cartridge being retained by the back plate, to dispense the components simultaneously from the containers through the outlet and static mixer to the outlet tip. In this embodiment, the actuators are controlled by a computer for precise mixing and delivery as desired. Moreover, a plurality of outlets can be provided so that a plurality of patient areas can be injected in parallel.

The most widely used material for scaffolding and tissue engineering is hyaluronic acid. This material is a major constituent of the extracellular matrix (ECM), and is the only non-sulfated glycosaminoglycan (GAG). This poly-anionic molecule is ubiquitous, biocompatible, biodegradable, and performs many important biological functions.

Some of these functions are:
stabilizing and organizing the ECM
regulating cell adhesion
motility [35,36],
mediating cell proliferation
and differentiation.

The molecular weight of HA can get very high, as high as a few million Daltons. This fact along with its biocompatibility nature makes HA is an ideal scaffolding material and tissue engineering material only if did not biodegrade so fast. How quick it biodegrades depends on the specie and the anatomical location. The half-life degradation range of HA is between 1 day to several days. Through chemistry, the biodegradation of HA may be interfered with or slowed down through cross-linking. Conventional chemistry to cross-link HA yields cross-link HA molecule that has non-Newtonian properties making it very difficult to deliver it to the intended target. As discussed earlier in the background section, the best method to use HA in an augmentation application is to cross-link it in-situ inside the body at the target site.

There are several methods to cross-link HA in-situ, and they vary in their detrimental impacts on the neighboring tissue in-vivo. Four in-situ methods are summarized here, and the biocompatibility tests to characterize the impact of the process steps of these cross-linking methods showed that they were able to meet the requirements for the biocompatibility and that the cross-linking reactions and their by-products were not detrimental to the respective surrounding tissues:

1. A 3-Thiopropanoyl hydrazide HA (HA-DTPH) derivative cross-linked with polyethylene glycol diacrylate is an efficient reaction that complete in approximately 9 minutes at a molar ratio of 2 to 1. In biocompatibility tests conducted to characterize the in-situ process, there was no significant adverse event observed or recorded. The figure below shows a chemical structure of an a, b unsaturated esters and amides of PEG cross-linked with thiolated HA.

2. Other hydrazide methods include using the hydrazide chemistry described above for hydrogels that have been prepared using bishydrazide, trishydrazide, and polyvalent hydrazide compounds as cross-linkers. By adjusting the reaction conditions and the molar ratios of the reagents, gels with physicochemical properties ranging from soft-pourable gels to more mechanically-rigid and brittle gels could be obtained. HA-ADH can be cross-linked using commercially-available small molecule homobifunctional cross-linkers, shown the figure below.

D

3. HA may be cross-linked first by ex-situ using the glutaraldehyde method. Ion exchange is key component making this product functional. The hyaluronan strands are extruded from cation-exchanged sodium hyaluronate (1.6 MDa) were cross-linked in glutaraldehyde aqueous solution. The strand surfaces were then remodeled by attachment of poly-D- and poly-L-lysine. The polypeptide-resurfaced hyaluronan strands showed good biocompatibility and promoted cellular adhesion.
4. Photo cross-linking is another method to cross-link HA using a methacrylate derivative of hyaluronan was synthesized by the esterification of the hydroxyls with excess methacrylic anhydride, as described above for hyaluronan butyrate. This derivative was photo-cross-linked to form a stable hydrogel using ethyl eosin in 1-vinyl-2-pyrrolidone and triethanolamine as an initiator under argon ion laser irradiation at 514 nm. The use of in situ photo-polymerization of an hyaluronan derivative, which results in the formation of a cohesive gel enveloping the injured tissue, may provide isolation from surrounding organs and thus prevent the formation of adhesions. A preliminary cell encapsulation study was successfully performed with islets of Langerhans to develop a bio-artificial source of insulin.

Preferably, the cross linker is non-toxic and safe for human use. In one embodiment, the cross linker improves the resistance of HA in the human body to mechanical degradation by contacting at least a portion of a HA with an effective amount of a crosslinking reagent. In one embodiment, a method of curtailing the progressive mechanical degradation of HA by enhancing the body's own efforts to stabilize the HA material by increasing collagen crosslinks. In this embodiment, this mechanical degradation may be in response to physiologic levels of repetitive loading. The crosslinking reagent is not particularly limited. Any crosslinking reagent known to be substantially non-cytotoxic and to be an effective cross-linker of collagenous material may be used. The crosslinking reagent is required to be substantially non-cytotoxic in order to facilitate direct contact of the crosslinking agent to tissues in the living human body. Preferably, the crosslinking reagent exhibits substantially less cytotoxicity compared to common aldehyde fixation agents. More preferably, a non-cytotoxic crosslinking reagent is used. Appropriate cytotoxicity testing will be used to verify the minimal cytotoxicity of candidate crosslinking reagents prior to use in humans. Tissue specific in vitro tests of cytotoxicity, of the standard form applied to mouse connective tissue (F895-84(2001)e1 Standard Test Method for Agar Diffusion Cell Culture Screening for Cytotoxicity), or Chinese Hamster Ovaries (ASTM E1262-88 (1996) Standard Guide for Performance of the Chinese Hamster Ovary Cell/Hypoxanthine Guanine Phosphoribosyl Transferase Gene Mutation Assay) preferably utilizing cell lines from tissues approximating the fibrous and gelatinous tissues of the intervertebral disc, should be conducted to evaluate the level of toxicity of any specific combination of crosslinking reagents known to have minimal cytotoxicity. These in vitro tests should similarly be followed by in vivo animal tests prior to use in humans.

The crosslinking reagent includes at least one crosslinking agent. The crosslinking agent chosen in accordance with the present invention is an effective cross-linker of collagenous material. When used in a cross-linking reagent, an effective crosslinker is one that increases the number of crosslinks in the HA when the crosslinker is brought into contact with a portion of the HA. An effective crosslinker improves the fatigue resistance of the treated HA, reduces material property degradation resulting from repetitive physiologic loading, or reduces the increase of viscoelastic properties of the treated tissue due to fatigue loading. Likewise, an effective crosslinker may reduce the decrease in elastic-plastic properties due to fatigue loading of the treated tissue. In one embodiment of the present invention, the crosslinking agent can be Genipin, a substantially non-toxic, naturally occurring crosslinking agent. Genipin is obtained from its parent compound, geniposide, which may be isolated from the fruits of *Gardenia jasminoides*. Genipin may be obtained commercially from Challenge Bioproducts Co., Ltd., 7 Alley 25, Lane 63, TzuChiang St. 404 Taichung Taiwan R.O.C., Tel 886-4-3600852. In another embodiment of the present invention, the crosslinking agent is a bioflavonoid, and more specifically, the bioflavonoid is proanthrocyanidin. A mixture containing proanthrocyanidin can be obtained as MegaNatural™ Gold from Polyphenolics, Inc, 22004 Rd. 24, Medera, Calif. 93638, Tel 559-637-5961. More than one crosslinking agent may be used. Appropriate cross-linking reagents will also include sugars such as ribose or threose, lysyl oxidase (LO) enzyme, an LO promoter, an epoxy and a carbodiimide. These agents have been used in Patent Application 20040253219 to stabilize discs in scoliotic spines by increasing collagen crosslinks, the content of which is incorporated by reference.

The crosslinking reagent may include a carrier medium in addition to the crosslinking agent. The crosslinking agent may be dissolved or suspended in the carrier medium to form the crosslinking reagent. In one embodiment, a crosslinking agent is dissolved in a non-cytotoxic and biocompatible carrier medium. The carrier medium is required to be substantially non-cytotoxic in order to mediate the contact of the crosslinking agent to tissues in the living human body without substantial damage to the tissue or surrounding tissue. Preferably, the carrier medium chosen is water, and more preferably, a saline solution. Preferably, the pH of the carrier medium is adjusted to be the same or similar to the tissue environment. Even more preferably, the carrier medium is buffered. In one embodiment of the present invention, the carrier medium is a phosphate buffered saline (PBS).

When the crosslinking agent is dissolved in a carrier medium, the concentration of the crosslinking agent in the carrier medium is not particularly limited. The concentration may be in any amount effective to increase the crosslinking of the tissue while at the same time remaining substantially noncytotoxic.

In accordance with the present invention, the crosslinking reagent is brought into contact with a portion of a collagenous tissue. As used herein, collagenous tissue is defined to be a structural or load supporting tissue in the body comprised of a substantial amount of collagen. Examples would include intervertebral disc, articular cartilage, ligament, tendon, bone, and skin. In general, the portion of the collagenous tissue to be brought into contact with the crosslinking reagent is the portion of the tissue that is subject to loading. Further, where at least some degradation of the collagenous tissue has occurred, the portion of the tissue to be contacted with the crosslinking reagent is at least the portion of the tissue that has been degraded. Preferably, the entire portion that is subject to loading or the entire portion that is degraded is contacted with the crosslinking reagent. Further, the tissue adjacent the portion of collagenous tissue subject to the loading may also be contacted with the crosslinking reagent.

The selected portion of the collagenous tissue must be contacted with an effective amount of the non-toxic crosslinking reagent. An "effective amount" is an amount of crosslinking reagent sufficient to have a mechanical effect on the portion of the tissue treated. Specifically, an "effective amount" of the crosslinking reagent is an amount sufficient to improve the fatigue resistance of the treated tissue, reduce material property degradation resulting from repetitive physiologic loading, or reduce the increase of viscoelastic properties of the treated tissue due to fatigue loading, or reduce the decrease of elastic-plastic properties of the treated tissue due to fatigue loading.

The method of the present invention includes contacting at least a portion of the HA or patient tissue with an effective amount of the crosslinking reagent. The contact may be affected in a number of ways. Preferably, the contacting of HA or collagenous tissue is affected by a means for minimally invasive delivery of the non-cytotoxic crosslinking reagent. Preferably, the contact between the tissue and the crosslinking reagent is effected by injections directly into the select tissue using a needle. Preferably, the contact between the tissue and the crosslinking reagent is effected by injections from a single or minimum number of injection locations. Preferably, an amount of crosslinking solution is injected directly into the targeted tissue using a needle and a syringe. Preferably, a sufficient number of injections are made along the portion of the tissue to be treated so that complete coverage of the portion of the collagenous tissue to be treated is achieved.

Alternatively, contact between the tissue and the crosslinking reagent is affected by placement of a time-release delivery system or temperature release deliver system directly into or onto the target tissue. One time-released delivery system that may be used is a treated membrane or patch. A reagent-containing patch may be rolled into a cylinder and inserted percutaneously through a cannula to the tissue sight, unrolled and using a biological adhesive or resorbable fixation device (sutures or tacks) be attached to the periphery of the targeted tissue.

Another time-released delivery system that may be used is a gel or ointment. A gel or ointment is a degradable, viscous carrier that may be applied to the exterior of the targeted tissue. Contact also may be effected by soaking or spraying, such as intra-capsular soaking or spraying, in which an amount of crosslinking solutions could be injected into a capsular or synovial pouch.

It should be noted that the methods and compositions treated herein are not required to permanently improve the resistance of collagenous tissues in the human body to mechanical degradation. The contacting may be repeated periodically to maintain the increased resistance to fatigue. For some treatment, the time between contacting is estimated to correspond to approximately 1 year for some individuals. Therefore, with either a single treatment or with repeated injections/treatments, the method of the present invention minimizes mechanical degradation of the collagenous tissue over an extended period of time.

Bioflavinoids and geniposides can be effective crosslinkers with minimal cytotoxicity. Similarly, sugar (e.g., ribose or threose) solutions have been shown to increase the number of non-enzymatic glycation produced crosslinks (naturally produced crosslinks, pentosidine is one example). Lysyl oxidase is the naturally produced enzyme involved in the formation of immature and mature endogenous (naturally occurring) collagen crosslinks. The method used to increase the crosslinking HA or surrounding tissue may include directly contacting living human tissue with appropriate concentrations of minimally-cytotoxic crosslinking reagents such as genipin (a geniposide) or proanthocyanidin (a bioflavinoid) or a sugar such as ribose or threose, or lysyl oxidase (LO) enzyme, or a LO promoter, or an epoxy or a carbodiimide.

A treatment method according to this embodiment incorporates a means for minimally invasive delivery of the non-cytotoxic crosslinking reagent such as placement of a time-release delivery system such as an imbedded pellet or time release capsule, or a treated membrane or patch directly into or onto the target tissue. Additional, guidable, arthroscopic-types of devices may be developed to facilitate application of the reagents to appropriate areas on the intervertebral discs or adjacent bony, capsular or ligamentous tissues.

A major limitation of most scaffold materials used for tissue engineering is the need for surgical implantation. For many clinical uses such as anatomical aesthetic augmentation of the body such as various areas on the face, the breast, butt or body, and the buttock, injectable in situ cross-linkable hydrogels such as hyaluronic acid (HA) would be strongly preferred for three main reasons.

1. In-Situ Reaction, an injectable material could be formed into any desired shape at the site of injury. Because the initial materials could be sol gels or moldable putties, the systems may be positioned in complex shapes and then subsequently cross-linked to conform to the required dimensions.

2. Mechanical Attachment, the cross-linkable polymer mixture would adhere to the tissue during gel formation, and the resulting mechanical interlocking that would arise from surface micro-roughness would strengthen the tissue-hydrogel interface.

3. Minimal Invasiveness, of an in situ cross-linkable hydrogel could be accomplished by injection or laparoscopic methods, thereby minimizing the invasiveness of the procedure. For many clinical uses such as anatomical aesthetic augmentation of the body such as various areas on the face, the breast, butt or body, and the buttock, injectable in situ cross-linkable hydrogels such as hyaluronic acid (HA) would be strongly preferred for three main reasons.

Figure 2:
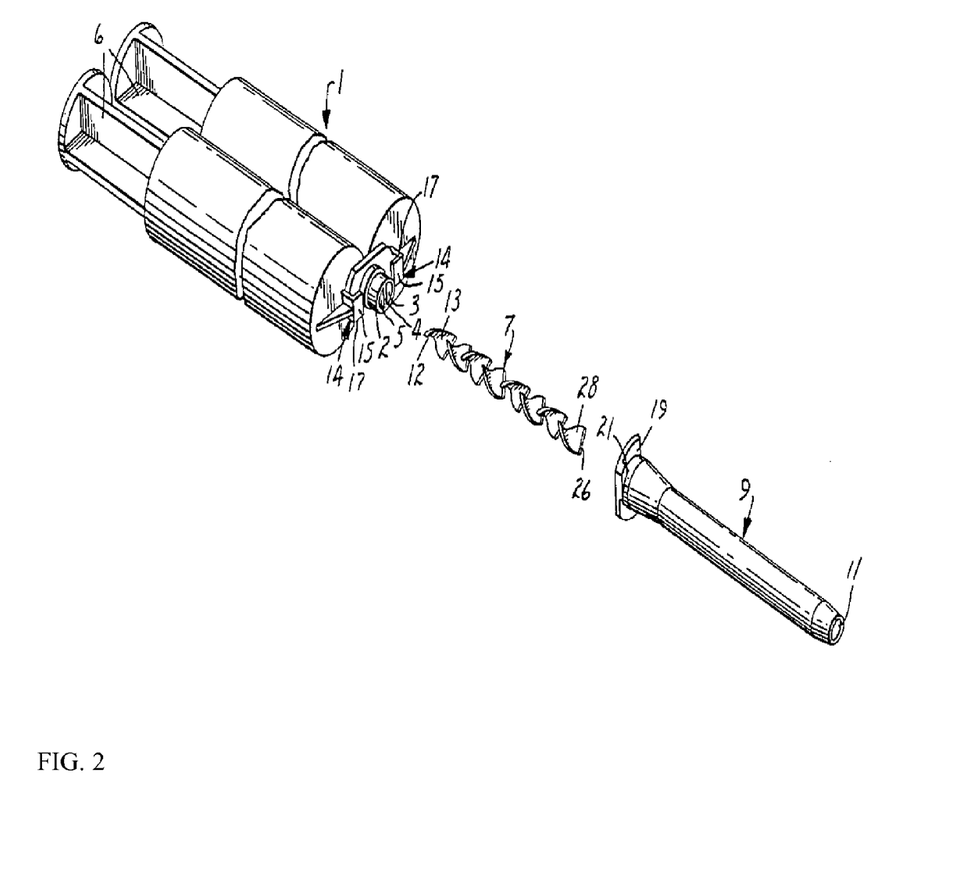
FIGS. 2-3 shows an exemplary manual hyaluronic acid (HA) injector system that cross-links the HA while the drug is injected into the body.

Referring now to FIG. 2, there is shown an exploded view in perspective of a static mixing device for forming cross-linked HA as it is injected into the patient. Although illustrated as a dual chamber device, syringe 1 has two or three parallel internal chambers, each of which is intended to be filled with a cross-linked material such as DVS, a filler material such as hyaluronic acid, and a catalyst such as sodium bicarbonate solute. The chambers in syringe 1 are separated by barrier 4. When a pair of plungers 6 are forced into the chambers in syringe 1, the contents of the syringe exit via outlet 2 through outlet passages 3 and 5, flow through static mixing element 7 and exit conduit 9, and are intimately mixed to form a homogeneous mass which will rapidly polymerize following expulsion from outlet 11 of exit conduit 9. Static mixing element 7 is prevented from being expelled during use from the outlet end of exit conduit 9 by a suitable constriction in the inside diameter of exit conduit 9 proximate its outlet end.

In one embodiment, maximum efficiency of mixing is obtained by insuring that the inlet end 12 of the first mixing blade 13 of static mixing element 7 is generally perpendicular to the plain of contiguity between the two resin streams exiting syringe 1 through exit passages 3 and 5. Such perpendicular orientation is obtained using a locating tang in exit conduit 9, which locating tang serves to orient static mixing element 7 with respect to syringe 1.

Rotational alignment of exit conduit 9 with respect to syringe 1 is obtained using a suitable mounting means (e.g., a bayonet mount). Bayonet locking tabs 14 have locking prongs 15 and stop surfaces 17. Exit conduit 9 has locking ramps 19 and stop surfaces 21. Exit conduit 9 is mounted on syringe 1 by centering the inlet of exit conduit 9 over outlet 2 of syringe 1, while aligning exit conduit 9 so that it can be pushed between bayonet locking tabs 14. Exit conduit 9 is then inserted firmly over outlet 2, and rotated approximately 90° clockwise (as viewed from the exit end of the conduit) so that locking ramps 19 are wedged between locking prongs 15 and the main body of syringe 1, and stop surfaces 17 engage stop surfaces 21.

When so mounted, exit conduit 9 is fixably rotationally aligned with respect to syringe 1. In addition, through locating means described in more detail below, static mixing element 7 is fixably rotationally aligned with respect to exit conduit 7 and syringe 1. Static mixing element 7 and exit conduit 9 are firmly attached to syringe 1, but can be readily removed and discarded after use by rotating exit conduit 9 approximately 90° counterclockwise (as viewed from the exit end of the conduit) and pulling exit conduit 9 away from syringe 1.

Syringe 1, exit nozzle 2, exit passages 3 and 5, barrier 4, plungers 6, static mixing element 7, exit conduit 9, inlet edge 12, first mixing blade 13, bayonet locking tabs 14, and locking prongs 15 are as in FIG. 1. Static mixing element 7 is rotationally aligned within exit conduit 9 by one or more guides proximate the outlet end of exit conduit 9. Guides 24 and 25 are small inward projections in the bore of exit conduit 9, and have a "fish mouth" appearance when viewed in perspective. When viewed in isolation, locking guides 24 and 25 each resemble the nib of a fountain pen.

When static mixing element 7 is inserted into the inlet end of exit conduit 9, and pushed toward the outlet end of exit conduit 9, guides 24 and 25 serve to rotationally align static mixing element 7 within exit conduit 9. When leading edge 26 of the final mixing blade 28 of static mixing element 7 approaches the outlet end of exit conduit 9, guides 24 and 25 cause static mixing element 7 to rotate about its long axis until leading edge 26 abuts edge surface 24a of guide 24 or edge surface 25a of guide 25.

When a static mixing element is inserted sufficiently far into exit conduit 9 to strike cusp 33, the leading edge of the static mixing element is deflected by cusp 33 toward edge surface 24a or toward edge surface 24b, thereby providing the desired rotational alignment. Depending upon whether the static mixing element abuts against edge surface 24a or 24b of guide 24 (and against corresponding edge surface 25b or 25a of guide 25), the final orientation of the static mixing element will be in one of two positions, each of those positions being 180° of rotation apart from the other. Each position is equally acceptable as a means for optimizing the efficiency of the first blade of the static mixing element, since in either position the first mixing element will intersect the incoming streams of resin at an approximate right angle to the plane of contiguity between the incoming streams and subdivide the incoming streams equally.

Although FIG. 2 shows two chambers 4, one embodiment provides three chambers 4: a first chamber containing a cross-linking material such as DVS, a second chamber containing hyaluronic acid (HA), and a third chamber containing a catalyst such as sodium bicarbonate solution.

The inner content 6 of the implant is a composition that is composed mainly of hyaluronic acid. The term "hyaluronic acid" is used in literature to mean acidic polysaccharides with different molecular weights constituted by residues of D-glucuronic and N-acetyl-D-glucosamine acids, which occur naturally in cell surfaces, in the basic extracellular substances of the connective tissue of vertebrates, in the synovial fluid of the joints, in the endobulbar fluid of the eye, in human umbilical cord tissue and in cocks' combs. The term "hyaluronic acid" is in fact usually used as meaning a whole series of polysaccharides with alternating residues of D-glucuronic and N-acetyl-D-glucosamine acids with varying molecular weights or even the degraded fractions of the same, and it would therefore seem more correct to use the plural term of "hyaluronic acids". The singular term will, however, be used all the same in this description; in addition, the abbreviation "HA" will frequently be used in place of this collective term. HA can also be defined as an unsulphated glycosaminoglycan composed of repeating disaccharide units of N-acetylglucosamine (GlcNAc) and glucuronic acid (GlcUA) linked together by alternating beta-1,4 and beta-1,3 glycosidic bonds. Hyaluronic acid is also known as hyaluronan, hyaluronate, or HA. The terms hyaluronan and hyaluronic acid are used interchangeably herein. More details on how to make the HA are discussed in commonly owned, co-pending application Ser. No. 13/353,316, filed Jan. 18, 2012, and entitled "INJECTABLE FILLER," the content of which is incorporated by reference.

Figure 3:
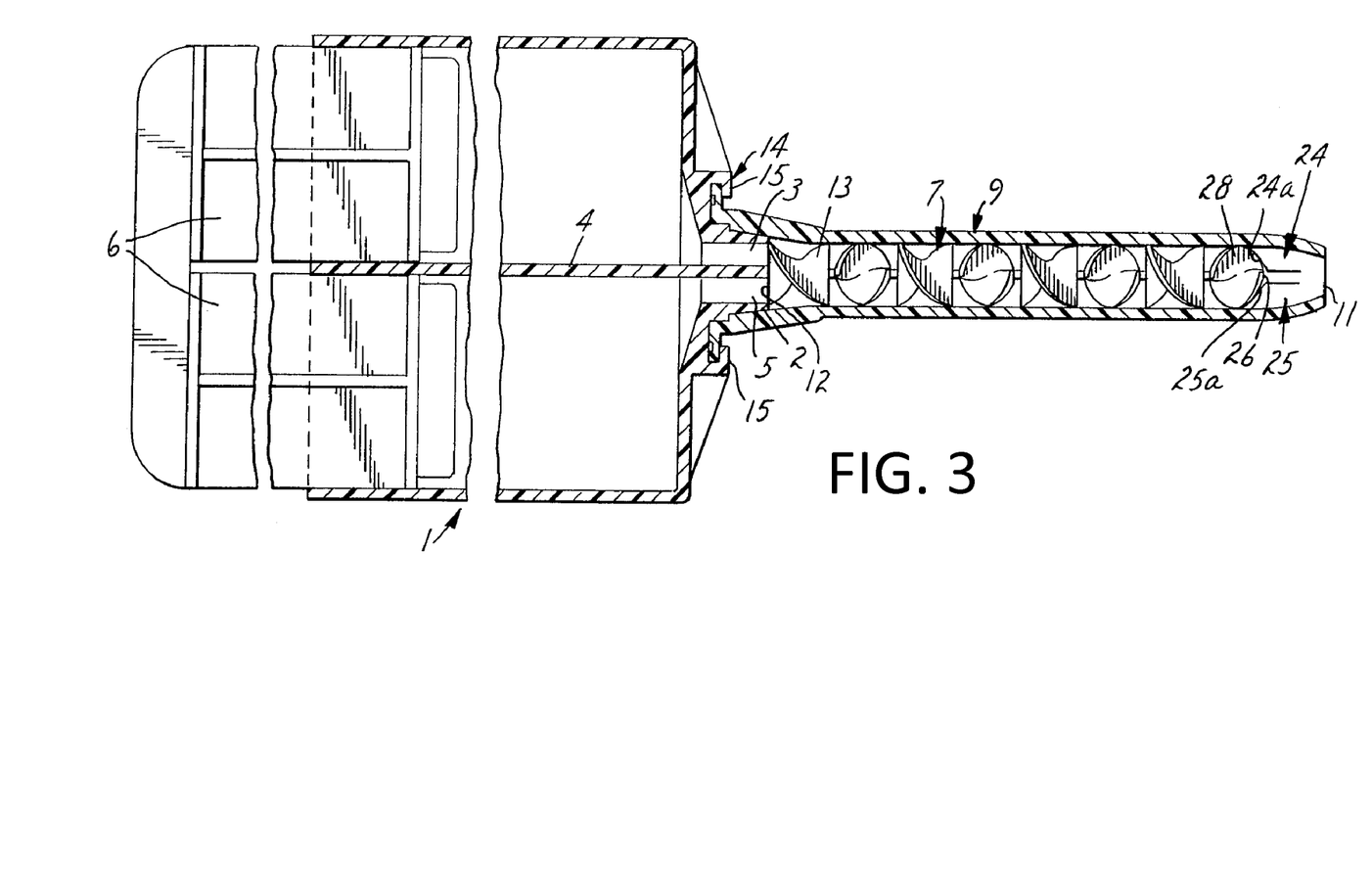
Figure 4:
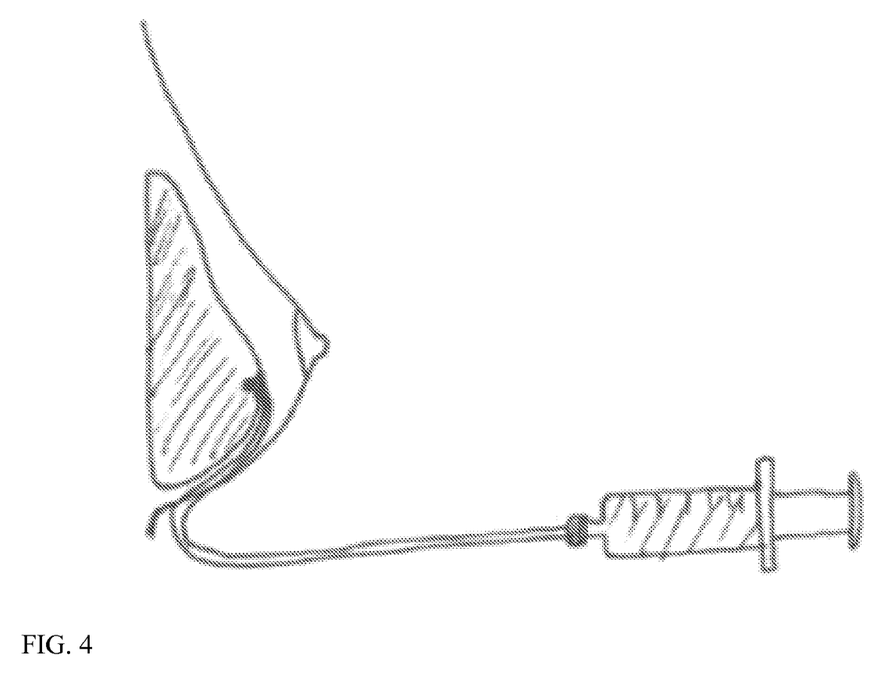
FIG. 4 shows an exemplary breast, butt or body implant delivery system.

The injectors of FIG. 1 or FIGS. 2-3 can be used to inject HA for dermal filling or for filling a breast, butt or body implant, as shown in FIG. 4.

Figure 5:
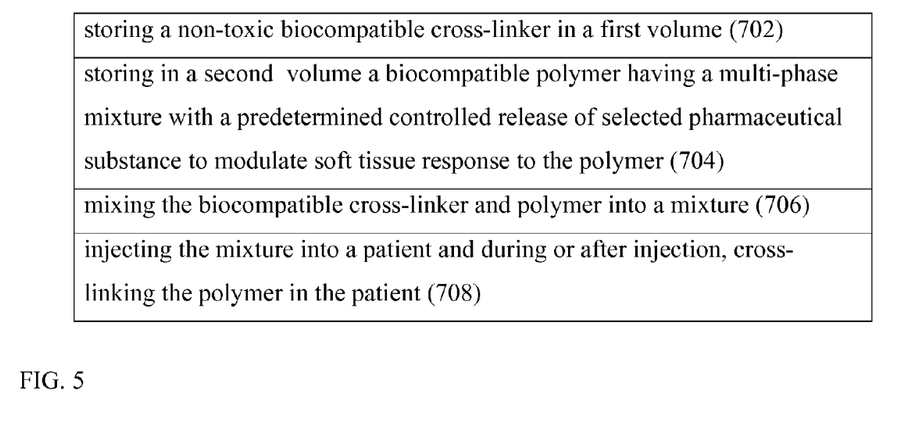
FIG. 5 shows an exemplary process to inject and cross-link materials at the same time.

FIG. 5 shows an exemplary process to inject and cross-link materials at the same time. The process includes storing a non-toxic biocompatible cross-linker in a first volume (702); storing in a second volume a biocompatible polymer having a multi-phase mixture with a predetermined controlled release of selected pharmaceutical substance to modulate soft tissue response to the polymer (704); mixing the biocompatible cross-linker and polymer into a mixture (706); and injecting the mixture into a patient and during or after injection, cross-linking the polymer in the patient (708).

Figure 6:
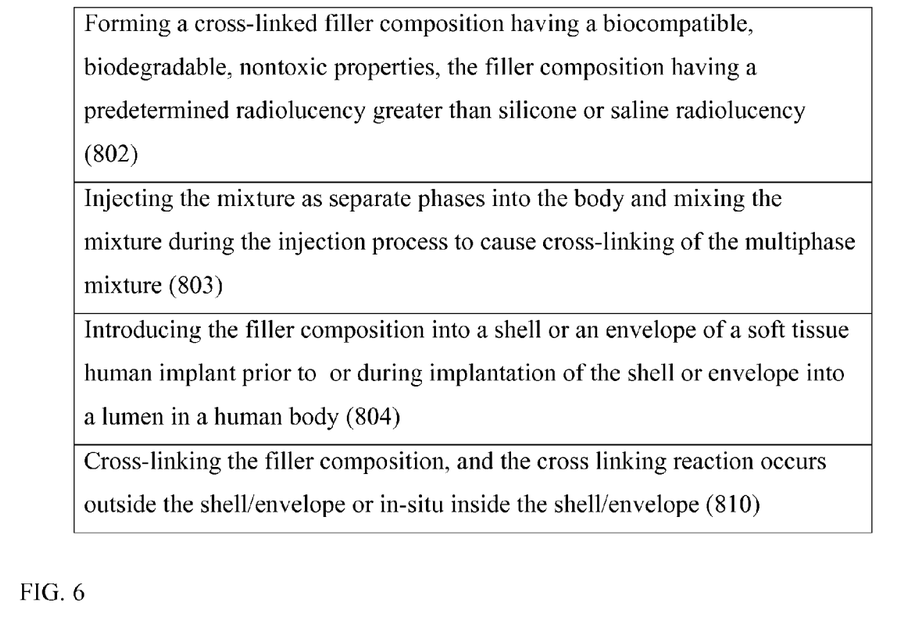
FIG. 6 shows another exemplary process to inject and cross-link materials at the same time.

FIG. 6 shows another exemplary process to inject and cross-link materials at the same time. The process includes forming a cross-linked filler composition having a biocompatible, biodegradable, nontoxic properties, the filler composition having a predetermined radiolucency greater than silicone or saline radiolucency (802). The process also injects the mixture as separate phases into the body and mixing the mixture during the injection process to cause cross-linking of the multiphase mixture (803). The filler composition with HA and cross linking materials is introduced into a shell or an envelope of a soft tissue human implant prior to or during implantation of the shell or envelope into a lumen in a human body (804). The cross-linking the filler composition occurs, and the cross linking reaction occurs outside the shell/envelope or in-situ inside the shell/envelope (810).

With certain HAs, the cross linking of the HA external to the shell can cause the cross-linked gel to become hardened and thus the HA may not be inserted into the shell easily with desired properties. A reversible cross-linking system can be used in one embodiment, where the cross links will be labile at extreme pH values, and at physiological pH, the cross-links become fixed. Two product streams can enter the shell, one is the product at an altered pH state and the other is the PBS, the neutralizer.

In the above processes, biocompatible reactants react in-situ to alter the physical properties a biocompatible polymer intended for said purpose from a deformable state to a non-deformable state. This polymer is a multi-phase mixture with a predetermined controlled release of selected pharmaceutical substances to modulate the response of the body to the polymer.

Gelling by either bioresponsive self-assembly or mixing of binary crosslinking systems, these technologies are useful in minimally invasive applications as well as drug delivery systems in which the sol-to-gel transition aids the formulation's performance. Moreover, not only does the chemical nature of the crosslinking moieties allow these systems to perform in situ, but they contribute dramatically to the mechanical properties of the hydrogel networks. For example, reversible crosslinks with finite lifetimes generate dynamic viscoelastic gels with time-dependent properties, whereas irreversible crosslinks form highly elastic networks.

The intrinsic properties of in situ forming gels add a new dimension of flexibility to large space augmentation such as that of the breast, butt or body and the buttock. While the silicone filled shell gives the feel and touch of native tissue, the long term health and legal complications associated of foreign body reaction and biocompatibility cannot be avoided. The over the lifetime of the implant, the fact that silicone fluid finding its way to the tissue on the outside of the shell is a kinetic eventuality. Saline filled shell has been a reluctant alternative because its feel and aesthetic affect are far from natural. The best of both worlds alternative might be found in a native material such as hyaluronic acids. The required properties might be best satisfied in an in situ crosslinked hyaluronic acid, or ex situ crosslinked hyaluronic acid or super high molecular weight linear (uncrosslinked) hyaluronic acids.

The following are examples of in situ crosslinking method for hyaluronic acids:

1. Hyaluronic acids, hydrazide and aldehyde:

Doubly crosslinked networks composed of HA microgels and crosslinked hydrogels with tunable is coelasticity in the relevant frequency range have been proposed for vocal fold healing. These partially monolithic and partially living materials feature divinylsulfone-crosslinked HA particles that have been oxidized with periodate to produce surface aldehyde functionalities.

A derivative of hyaluronic acid (HA), comprising the steps of:

1.1. forming an activated ester at a carboxylate of a glucuronic acid moiety of hyaluronic acid;

1.2. substituting at the carbonyl carbon of the activated ester formed in step 1.1

1.3. a side chain comprising a nucleophilic portion and a functional group portion; and 1.4. forming a cross-linked hydrogel from the functional group portion of the hyaluronic acid derivative in solution under physiological conditions wherein the forming of a cross-linked hydrogel is not by photo-cross-linking.

2. Hyaluronic acid, dextran by forming a hydrazine

3. Functionalization of hyaluronic acid (HA) with chemoselective groups enables in situ formation of HA-based materials in minimally invasive injectable manner. One embodiment of HA modification with such groups primarily rely on the use of a large excess of a reagent to introduce a unique reactive handle into HA and, therefore, are difficult to control. FIG. 9 shows another embodiment with a protective group strategy based on initial mild cleavage of a disulfide bond followed by elimination of the generated 2-thioethoxy-carbonyl moiety ultimately affording free amine-type functionality, such as hydrazide, aminooxy, and carbazate. Specifically, new modifying homobifunctional reagents may be synthesized that contain a new divalent disulfide-based protecting group. Amidation of HA with these reagents gives rise to either one-end coupling product or to intra/intermolecular cross-linking of the HA chains. However, after subsequent treatment of the amidation reaction mixture with dithiothreitol (DTT), these cross-linkages are cleaved, ultimately exposing free amine-type groups. The same methodology was applied to graft serine residues to the HA backbone, which were subsequently oxidized into aldehyde groups. The strategy therefore encompasses a new approach for mild and highly controlled functionalization of HA with both nucleophilic and electrophilic chemoselective functionalities with the emphasis for the subsequent conjugation and in situ cross-linking. A series of new hydrogel materials were prepared by mixing the new HA-aldehyde derivative with different HA-nucleophile counterparts. Rheological properties of the formed hydrogels were determined and related to the structural characteristics of the gel networks. Human dermal fibroblasts remained viable while cultured with the hydrogels for 3 days, with no sign of cytotoxicity, suggesting that the gels described in this study are candidates for use as growth factors delivery vehicles for tissue engineering applications.

4. The gelation is attributed to the Schiff base reaction between amino and aldehyde groups of polysaccharide derivatives. In the current work, N-succinyl-chitosan (S-CS) and aldehyde hyaluronic acid (A-HA) were synthesized for preparation of the composite hydrogels.

5. FIG. 10 shows injectable hyaluronic acid (HA) hydrogels cross-linked via disulfide bond are synthesized using a thiol-disulfide exchange reaction. The production of small-molecule reaction product, pyridine-2-thione, allows the hydrogel formation process to be monitored quantitatively in real-time by UV spectroscopy. Rheological tests show that the hydrogels formed within minutes at 37° C. Mechanical properties and equilibrium swelling degree of the hydrogels can be controlled by varying the ratio of HA pyridyl disulfide and macro-cross-linker PEG-dithiol. Degradation of the hydrogels was achieved both enzymatically and chemically by disulfide reduction with distinctly different kinetics and profiles. In the presence of hyaluronidase, hydrogel mass loss over time was linear and the degradation was faster at higher enzyme concentrations, suggesting surface-limited degradation.

The viscosity of these polymers could be controlled by using its pH properties. The low viscosity region during low pH environment helps with deployment of the augmentation gel because the gel has to be delivered through a small diameter tubing. Polymers that are pH sensitive are also called polyelectrolytes. The swelling properties of polyelectrolyte networks, which can be described in terms of the swelling rate and maximum solution uptake at equilibrium, depend on the physicochemical properties of the polymers and on the composition of the surrounding medium. Polyelectrolyte gels change their conformation with the degree of dissociation which is the function of quantities such as pH value, polarity of the solvent, ionic strength and temperature of the external environment solution.

Example C

Another preferred embodiment is filling a silicone shell with cross-linked hyaluronic acid material. This method required a high sheer mixer. The HA is cross linked using available cross-linkers such as divinyl sulfone, 1,4-butane diol diglycidyl ether in the presence of 0.1M sodium hydroxide. When the crosslinking reaction has completed, the HA gel is washed repeatedly until the residual cross-linker was no longer detectable in the HA gel, At this point, the cross-linked gel is blended with 10% water in shear mode to create uniform and small particles. The blended cross-linked material reformulated with un-cross-linked materials HA for injectability and longevity.

The implants of the present invention further can be instilled, before or after implantation, with indicated medicines and other chemical or diagnostic agents. Examples of such agents include, but are not limited to, antibiotics, chemotherapies, other cancer therapies, brachytherapeutic material for local radiation effect, x-ray opaque or metallic material for identification of the area, hemostatic material for control of bleeding, growth factor hormones, immune system factors, gene therapies, biochemical indicators or vectors, and other types of therapeutic or diagnostic materials which may enhance the treatment of the patient.

The present invention has been described particularly in connection with a breast, butt or body implant, but it will be obvious to those of skill in the art that the invention can have application to other parts of the body, such as the face, and generally to other soft tissue or bone. Accordingly, the invention is applicable to replacing missing or damaged soft tissue, structural tissue or bone, or for cosmetic tissue or bone replacement.

Although the present invention has been described in relation to particular embodiments thereof, many other variations and modifications and other uses will become apparent to those skilled in the art. It is preferred, therefore, that the present invention be limited not by the specific disclosure herein, but only by the appended claims. The other methods, used for characterization of the products according to one embodiment are described in the following examples which illustrate preferred embodiments of one embodiment without, however, being a limitation thereof. Variations and modifications can, of course, be made without departing from the spirit and scope of the invention.

What is claimed is:

1. A method for cosmetic augmentation, comprising:
   characterizing a target tissue,
   maintaining a consistency of a biocompatible polymer in particle size and population density to match the target tissue by forming the biocompatible polymer with an average molecular weight and a polydispersity index;
   storing a non-toxic biocompatible cross-linker;
   storing a biocompatible polymer having a multi-phase mixture with a predetermined controlled release of a selected pharmaceutical substance to modulate soft tissue response to the polymer;
   mixing the biocompatible cross-linker and polymer into a mixture and cross-linking the polymer; and reversibly cross-linking the polymer, where the cross links are labile at high pH values, and at physiological pH, the cross-links become fixed;
   augmenting soft tissue with the biocompatible cross-linked polymer having a predetermined radiolucency greater than silicone or saline radiolucency; and
   releasing the selected pharmaceutical substance over time to modulate soft tissue response to the polymer.

2. The method of claim 1, comprising introducing the polymer into a breast implant shell of a soft tissue human implant prior to or during implantation of the shell with a lumen in a human body.

3. The method of claim 1, comprising cross-linking the polymer, wherein a cross linking reaction occurs outside the shell or in-situ inside a breast implant shell.

4. The method of claim 1, wherein the polymer comprises one of: collagens, PEG, hyaluronic acids, celluloses, proteins, saccharides, biodegradable and bioresorbable biocompatible materials.

5. The method of claim 1, wherein the polymer comprises an extracellular matrix of a biological system.

6. The method of claim 1, comprising using cross linkers and forming homo-polymers or to form copolymers by crosslinking with other polymer species.

7. The method of claim 1, comprising adding a substance to the composition for biocompatibility.

8. The method of claim 1, comprising controlling drug releases at predetermined timing in anticipation of an onset of a negative physiological event in response to an invading foreign bodies.

9. The method of claim 1, comprising fast releasing, medium or slow releasing the composition.

10. The method of claim 1, comprising adding anesthetics, lidocaine or compound to reduce or eliminate acute inflammatory reactions to the pharmaceutical substance.

11. The method of claim 1, comprising adding one or more compositions selected from the group consisting of steroids, corticosteroids, dexamethasone, triamcinolone.

12. The method of claim 1, comprising providing an antiproliferative compound.

13. The method of claim 1, wherein the substance comprises paclitaxel, sirolimus.

14. The method of claim 1, comprising controlling a scar formation process around a foreign body including capsular formation.

15. The method of claim 1, comprising optimizing degradation profile of the composition.

16. The method of claim 1, comprising minimizing migration of the composition.

17. A method for cosmetic augmentation, comprising:
    maintaining a consistency of a biocompatible polymer in particle size and population density by forming the biocompatible polymer with an average molecular weight and a polydispersity index;
    storing a biocompatible polymer having a multi-phase mixture with a predetermined controlled release of a selected pharmaceutical substance to modulate soft tissue response to the polymer;

mixing the biocompatible cross-linker and polymer into a mixture and augmenting soft tissue with the biocompatible polymer;

reversibly cross-linking the polymer, where the cross links are labile at high pH values, and at physiological pH, the cross-links become fixed;

releasing the selected pharmaceutical substance over time to modulate soft tissue response to the polymer; and modeling a 3D model of a human body and continuously updating a display with a current shape of breast or butt from the 3D model including the injection to show fit to a desired shape.

18. The method of claim 1, comprising co-cross-linking glycosaminoglycan chemically with at least one other polymer including hyaluronan or hylan.

19. The method of claim 1, wherein the chemically cross-linked glycosaminoglycan is hyaluronan or hylan.

20. The method of claim 1, comprising in-situ non-covalent bonding including one of: hydrogen association, charge or ionic interactions, pH, osmolality.

21. A method for cosmetic augmentation, comprising:

maintaining a consistency of a biocompatible polymer in particle size and population density to match a target tissue by forming the biocompatible polymer with an average molecular weight and a polydispersity index;

storing a biocompatible polymer having a multi-phase mixture with a predetermined controlled release of a selected pharmaceutical substance to modulate soft tissue response to the polymer;

mixing the biocompatible cross-linker and polymer into a mixture and augmenting soft tissue with the biocompatible polymer;

releasing the selected pharmaceutical substance over time to modulate soft tissue response to the polymer; and modeling a 3D model of a human body and continuously updating a display with a current shape of breast or butt from the 3D model including the injection to show fit to a desired shape.

22. The method of claim 1, comprising injecting with a mechanical pump the biocompatible crosslinked polymer under soft tissue in a minimally invasive manner.

23. A method for cosmetic augmentation, comprising:

storing a non-toxic biocompatible cross-linker;

storing a biocompatible polymer having a multi-phase mixture with a predetermined controlled release of selected pharmaceutical substance to modulate soft tissue response to the polymer;

mixing the biocompatible cross-linker and polymer and injecting the mixture into a patient and reversibly cross-linking the polymer, where the cross links are labile at high pH values, and at physiological pH, the cross-links become fixed;

augmenting soft tissue with the biocompatible cross-linked polymer having a predetermined radiolucency greater than silicone or saline radiolucency; and releasing the selected pharmaceutical substance over time to modulate soft tissue response to the polymer.

* * * * *